United States Patent
Gilmore et al.

(10) Patent No.: US 6,939,941 B2
(45) Date of Patent: Sep. 6, 2005

(54) PREPARATION OF POLYSULFIDE COMPOSITIONS

(75) Inventors: John Richard Gilmore, Crystal Lake, IL (US); Keith Bradley Potts, Elgin, IL (US); Steven John Hobbs, Woodstock, IL (US); Marc Edward Halpern, Cherry Hill, NJ (US); Thomas Dennis Mundle, Mandevill, LA (US)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 10/228,731

(22) Filed: Aug. 27, 2002

(65) Prior Publication Data

US 2003/0050511 A1 Mar. 13, 2003

Related U.S. Application Data

(60) Provisional application No. 60/318,697, filed on Sep. 12, 2001.

(51) Int. Cl.$^7$ .............................................. C08G 75/14
(52) U.S. Cl. ...................... 528/389; 528/387; 528/373; 528/377; 528/482; 528/486; 568/21
(58) Field of Search ................................. 528/389, 387, 528/373, 397, 482, 486; 568/21

(56) References Cited

U.S. PATENT DOCUMENTS 5,430,192 A    7/1995   Hobbs et al.

FOREIGN PATENT DOCUMENTS

JP    56090835    12/1979
JP    04046931    6/1990

OTHER PUBLICATIONS

George R. Pettit, "Preparation of Elastothiomers with a Phase Transfer Catalyst," Journal of Polymer Science: Polymer Chemistry Edition, vol. 18, p. 345–347, 1980.

Tatsuro Matsui et. al., "Detection of a New Crosslinking and Properties of Liquid Polysulfide Polymer," Journal of Applied Polymer Science, vol. 71, p. 59–66, 1999.

Yoshio Imai et. al., "Synthesis of Aliphatic Polysulfides by Phase–Transfer–Catalyzed Polycondensation of Dibromoalkanes with Dithiols," Journal of Polymer Science: Polymer Letters Edition, v. 17, p. 579–583, 1979.

Mitsuru Ueda, et. al., "Synthesis of Poly(aliphatic sulfides) by Polycondensation of Sodium Sulfide with Dibromoalkanes in the Presence of quarternary Onium Salts," Macromolecules, v. 15, p. 248–251, 1982.

W. Mazurek et.al., "$^{13}$C NMR of Polysulfide Prepolymers," *Macromolecules*, vol. 24, p. 3261–3265, 1991.

*Primary Examiner*—Duc Truong
(74) *Attorney, Agent, or Firm*—DLA Piper Rudnick Gray Cary US LLP

(57) ABSTRACT

A process is provided for the manufacture of liquid polysulfide polymers. In particular, the process allows for making the liquid form of the polysulfide polymer directly and eliminates the need to first make a solid polysulfide polymer and then convert it to a liquid.

22 Claims, No Drawings

PREPARATION OF POLYSULFIDE COMPOSITIONS

CROSS REFERENCE TO RELATED PATENT APPLICATIONS

This is a non-provisional application of prior pending U.S. provisional application Ser. No. 60/318,697 filed Sep. 12, 2001.

BACKGROUND

This invention relates to a process for making liquid polysulfides, the liquid polysulfides made thereby, and sealants made therefrom.

Liquid polysulfides (LP's) have been available commercially for over thirty years. They are known to be polymers whose repeat units each contain an organic group and two adjacent sulfur atoms, represented by the chemical structure —(—S—S—R—)— where R is an organic group. The pair of adjacent sulfur atoms in this structure is called a "disulfide link." Details of suitable organic groups are described below. LP's include the usual variety of copolymers, branched structures, and end groups found in polymers of all types. Because they are liquids, they can be conveniently mixed and compounded with other materials, such as for example curing agents, cure accelerators or retarders, fillers, plasticizers, thixotropes, and adhesion promoters as appropriate for the application contemplated by the practitioner. LP's are used in a wide variety of applications, including for example in the manufacture of sealants for aircraft, insulating glass, and other items. The structure, the current methods of making LP's, the usual applications of LP's, and the corresponding formulations have all been described in "Polymers Containing Sulfur (Polysulfides)" by D. Vietti and M. Scherrer, in volume 19 of the *Kirk-Othmer Encyclopedia of Chemical Technology*, 4th edition, Wiley (1996).

LP's of the present invention are different from polymers known as "poly (aliphatic sulfide)" polymers or "aliphatic polysulfide" polymers or "poly (alkylene sulfide)" polymers or similar names, whose repeat units contain organic groups and sulfur atoms that are connected only to carbon atoms. That is, poly(aliphatic sulfide)s have repeat units such as for example —(—R—S—)— or —(—R—S—R'—S—)— where R and R' are organic groups. These polymers are described, for example, in Chapter 3 of *Polymer Synthesis Volume III* by S. R. Sandler and W. Karo (Academic Press, 1980). Such poly (aliphatic sulfide)s have been made in the past by reacting metal sulfides with dihalo organic compounds in the presence of a phase transfer catalyst, as reported for example in Japanese Patents JP04046931, to T. Tozawa et. al., and JP56090835, to Y. Kazuya; in Y. Imai et. al., *journal of Polymer Science*, volume 17, pages 579–583, 1979; and in M. Ueda et. at., *Macromolecules*, volume 15, pages 248–251, 1982. Both Tozawa and Ueda report that the presence of the phase transfer catalyst leads to an increase in the molecular weight of the polymers they produce.

The monomer units of the liquid polysulfides of the present invention are known to predominantly contain disulfide links. A liquid polysulfide polymer molecule may contain a small number of the aliphatic sulfide type monomer units. Generally, liquid polysulfide polymers are believed to have 80% or more of their total weight made of monomer units with disulfide links. Most samples of liquid polysulfide are believed to have 95% or more of their total weight made of monomer units with disulfide links.

In the past, liquid polysulfides have been produced, as described in U.S. Pat. 5,430,192, by first making a solid polysulfide polymer and then, in an extra step, converting the solid polymer to a liquid. During the making of the solid polysulfide polymer, an inorganic salt such as magnesium chloride is used. It is believed that the inorganic salt reacts with the sodium polysulfide to form colloidally suspended particles, on which the solid particles of organic polysulfide polymer grow. The resulting solid polysulfide polymer is thought to have relatively high molecular weight. The dispersion of solid polymer must be washed with water to remove impurities, which produces significant quantities of waste water. Next, the extra step converts this solid polymer to a liquid, by reacting the polymer with sodium dithionite and caustic or, more commonly, with sodium hydrosulfide (NaSH) and sodium sulfite ($Na_2SO_3$). This reaction is thought to reduce the molecular weight of the polymer, though it is also thought to be difficult to carefully control the precise value of the reduced molecular weight. After the molecular weight reduction, the extra-step process also requires a so-called "strip" step, in which the liquid polysulfide is reacted with more sodium sulfite, in order to remove labile sulfur from the polymer. Labile sulfur is sulfur that can be removed from the polymer by a relatively mild chemical reaction, such as for example the reaction with sodium sulfite. Then, to purify the product, the magnesium must be converted to a soluble salt by acidifying the reaction mixture, commonly with acetic acid or sodium bisulfite. Then the mixture must be washed with water to remove the soluble salts, producing further significant quantities of waste water. This extra-step process has the disadvantages of requiring extra time, effort, and materials, and of producing large amounts of waste water.

The problem addressed by the present invention is the provision of a simplified polymerization process for making liquid polysulfides directly, so that the extra step of converting a solid polysulfide to a liquid is no longer necessary. One further advantage of the present invention is that the elimination of the extra step also eliminates a significant amount of waste water from the LP manufacturing process. A second further advantage of the present invention is that elimination of the extra step also eliminates the need for the "strip" operation to remove labile sulfur, thus simplifying the manufacturing process and reducing the amount of sodium sulfite that must be removed from the liquid polysulfide. A third further advantage is that the present invention allows the practitioner to control the molecular weight of the LP without using the historical extra-step process.

SUMMARY OF THE INVENTION

In a first aspect of the present invention, there is provided a process for making liquid polysulfide compositions comprising reacting sodium polysulfide; at least one alpha, omega dihalo organic compound; and optionally at least one trihalo organic compound; wherein said reacting is performed in the presence of a phase transfer catalyst; wherein the group between the halogen atoms of said alpha, omega dihalo organic compound is selected from the list consisting of alkyl groups of 3 or more carbon atoms, aryl groups, alkylaryl groups, alkyloxy groups, and arylalkoxy groups; wherein the halogen atoms of said alpha, omega dihalo organic compound are selected from the group consisting of chlorine, bromine, and iodine; and wherein said process does not involve formation of solid polysulfide polymer.

In a second aspect of the present invention, there is provided a process for making liquid polysulfide compositions comprising (a) reacting sulfur and an aqueous solution of sodium hydrosulfide to form sodium polysulfide, (b) forming a liquid polysulfide by reacting said sodium polysulfide, at least one alpha, omega dihalo organic compound, and optionally at least one trihalo organic compound; wherein the group between the halogen atoms of said alpha, omega dihalo organic compound is selected from the list consisting of alkyl groups of 3 or more carbon atoms, aryl groups, alkylaryl groups, alkyloxy groups, and arylalkoxy groups; wherein the halogens of said alpha, omega dihalo organic compound are selected from the group consisting of chlorine, bromine, and iodine; and wherein said reacting is performed in the presence of a phase transfer catalyst; and (c) optionally reacting said liquid polysulfide with additional sulfur to raise the molecular weight of said liquid polysulfide; wherein said process does not involve formation of solid polysulfide polymer.

In a third aspect of the present invention, there is provided a liquid polysulfide composition made by a process comprising reacting sodium polysulfide, at least one alpha, omega dihalo organic compound, and optionally at least one trihalo organic compound; wherein said reacting is performed in the presence of a phase transfer catalyst; wherein the group between the halogen atoms of said alpha, omega dihalo organic compound is selected from the list consisting of alkyl groups of 3 or more carbon atoms, aryl groups, alkylaryl groups, alkyloxy groups, and arylalkoxy groups; wherein the halogen atoms of said alpha, omega dihalo organic compound are selected from the group consisting of chlorine, bromine, and iodine; and wherein said process does not involve formation of solid polysulfide polymer.

In a fourth aspect of the present invention, there is provided a liquid polysulfide composition made by a process comprising (a) reacting sulfur and an aqueous solution of sodium hydrosulfide to form sodium polysulfide;

(b) forming a liquid polysulfide by reacting said sodium polysulfide, at least one alpha, omega dihalo organic compound, and optionally at least one trihalo organic compound; wherein the group between the halogen atoms of said alpha, omega dihalo organic compound is selected from the list consisting of alkyl groups of 3 or more carbon atoms, aryl groups, alkylaryl groups, alkyloxy groups, and arylalkoxy groups; wherein the halogens of said alpha, omega dihalo organic compound are selected from the group consisting of chlorine, bromine, and iodine; and wherein said reacting is performed in the presence of a phase transfer catalyst; and (c) optionally reacting said liquid polysulfide with additional sulfur to raise the molecular weight of said liquid polysulfide; wherein said process does not involve formation of solid polysulfide polymer.

In a fifth aspect of the present invention, there is provided a solid polysulfide composition useful as a sealant made by a process comprising curing a liquid polysulfide composition made by the process comprising reacting sodium polysulfide, at least one alpha, omega dihalo organic compound, and optionally at least one trihalo organic compound; wherein said reacting is performed in the presence of a phase transfer catalyst; wherein the group between the halogen atoms of said alpha, omega dihalo organic compound is selected from the list consisting of alkyl groups of 3 or more carbon atoms, aryl groups, alkylaryl groups, alkyloxy groups, and arylalkoxy groups; wherein the halogen atoms of said alpha, omega dihalo organic compound are selected from the group consisting of chlorine, bromine, and iodine; and wherein said process does not involve formation of solid polysulfide polymer.

In a sixth aspect of the present invention, there is provided a solid polysulfide composition useful as a sealant made by a process comprising curing a liquid polysulfide composition made by a process comprising (a) reacting sulfur and an aqueous solution of sodium hydrosulfide to form sodium polysulfide;

(b) forming a liquid polysulfide by reacting said sodium polysulfide, at least one alpha, omega dihalo organic compound, and optionally at least one trihalo organic compound; wherein the group between the halogen atoms of said alpha, omega dihalo organic compound is selected from the list consisting of alkyl groups of 3 or more carbon atoms, aryl groups, alkylaryl groups, alkyloxy groups, and arylalkoxy groups; wherein the halogens of said alpha, omega dihalo organic compound are selected from the group consisting of chlorine, bromine, and iodine; and wherein said reacting is performed in the presence of a phase transfer catalyst; and (c) optionally reacting said liquid polysulfide with additional sulfur to raise the molecular weight of said liquid polysulfide; wherein said process does not involve formation of solid polysulfide polymer.

In a seventh aspect of the present invention, there is provided a sealant comprising a cured liquid polysulfide composition, wherein said liquid polysulfide is made by a process comprising reacting sodium polysulfide, at least one alpha, omega dihalo organic compound, and optionally at least one trihalo organic compound; wherein said reacting is performed in the presence of a phase transfer catalyst; wherein the group between the halogen atoms of said alpha, omega dihalo organic compound is selected from the list consisting of alkyl groups of 3 or more carbon atoms, aryl groups, alkylaryl groups, alkyloxy groups, and arylalkoxy groups; wherein the halogen atoms of said alpha, omega dihalo organic compound are selected from the group consisting of chlorine, bromine, and iodine; and wherein said process does not involve formation of solid polysulfide polymer.

DETAILED DESCRIPTION OF THE INVENTION

The present invention relates to liquid polysulfide polymers. By "liquid" we mean that the polysulfide is a liquid at room temperature, approximately 10° C. to approximately 40° C. We use the term "polymer" in its usual sense, meaning a molecule with many repeat units, as defined for example in *Textbook of Polymer Science*, 2nd edition, by F. W. Billmeyer, Jr., Wiley-Interscience (1971), including the usual variety of linear molecules, branched molecules, crosslinked molecules, various types of copolymers, etc. We use the term "polymer" to also include molecules with a relatively small number of repeat units, sometimes also called "oligomers."

The present invention involves sodium polysulfide, which has the chemical formula $Na_2S_n$, where n is thought to be in the range of from 2 to 5, with an average value between 2 and 2.5. The sodium polysulfide may be supplied in any convenient way; the source of the sodium polysulfide is not critical to the present invention. In one embodiment of the present invention, the sodium polysulfide is formed by reacting sulfur with an aqueous solution of sodium hydrosulfide. The same reaction between sulfur and NaSH is also thought to produce hydrogen sulfide ($H_2S$), which, for safety and environmental protection, should be trapped in some way, for example by bubbling through aqueous sodium hydroxide (NaOH) solution for conversion to NaSH. It is an advantage of this invention that the NaSH thus produced can be recycled as an ingredient in the production of LP.

Some embodiments of the present invention involve the use of sulfur. Sulfur is available in a variety of forms, including for example various powder forms, such as for example amorphous, bright, crude, dark, dusting, flour, flowers, ground, insoluble, precipitated, refined, screened, spray, and wettable. Sulfur is also available in the molten state; as a colloidal dispersion, also called flowable sulfur; and in other physical forms such as for example prills, granules, pellets, or flakes. The form of sulfur used is not critical to the present invention. Preferred is any powder form. More preferred is powder with purity higher than 99%. In some embodiments, an initial portion of sulfur is used during the formation of the sodium is polysulfide. In some embodiments, after the formation of the liquid polysulfide, an optional further portion of sulfur is added, to raise the molecular weight of the liquid polysulfide.

Some embodiments of the present invention also involve the use of an aqueous solution of sodium hydrosulfide. The preferred concentration of the NaSH solution is at least 10% by weight of NaSH on the total weight of the solution; more preferred is 25 to 50 weight %, and most preferred is 30 to 35 weight %. It is preferred to filter the NaSH solution before use. The preferred amount of NaSH is determined by the ratio of moles of NaSH to the moles of sulfur in the initial portion of sulfur used in the polymerization of the LP, excluding the sulfur in the optional further portion that may be added after the polymerization of the LP. The preferred ratio of moles of NaSH to moles of sulfur atoms in the initial portion of sulfur is in the range of from 1.5:1 to 7:1; more preferred is a range of from 3:1 to 5:1; and most preferred is 3.8:1 to 4.2:1.

In the present invention, another ingredient is at least one phase transfer catalyst (PTC) such as, for example, quaternary ammonium salts, phosphonium salts, and crown ethers. A more detailed description of phase transfer catalysis and descriptions of compounds suitable as phase transfer catalysts can be found in E. V. Dehmlow, "Catalysis, Phase Transfer," in volume 5 of the *Kirk-Othmer Encyclopedia of Chemical Technology*, 4th edition, Wiley (1996). Further examples of PTC's can be found in JP04046931, to T. Tozawa et. al. FTC's have been used in the past to produce solid rubber polysulfides using dihalo organic compounds that were either alpha, alpha dihalo or else alpha, beta dihalo organic compounds, as for example in G. Pettit, *J. Polym. Sci., Polym. Chem. Ed.*, v.18, p. 347 (1980). In the present invention, preferred phase transfer catalysts are tetrabutylammonium bromide, 18-crown-6, tetraphenylphosphonium halide, or methyltributylammonium chloride. Most preferred is methyltributylammonium chloride. A suitable amount of PTC is 0.01 to 10 mole % based on the moles of the alpha, omega dihalo organic compound or compounds, and a preferred amount is 0.05 to 2.0 mole %.

In the present invention, yet another ingredient is at least one alpha, omega dihalo organic compound. This compound has the chemical formula X—R—Y, where X and Y are halogens and R is an organic group. X and Y may be different halogen atoms or the same halogen atoms. By "alpha, omega" we mean that the halogen atoms are believed to be attached to opposite ends of the organic group. Suitable halogens are chlorine, bromine, and iodine. The preferred halogen is chlorine. Suitable organic groups are alkyl groups with 3 or more carbon atoms, aryl groups, alkylaryl groups, alkoxy groups, and arylalkoxy groups. Preferred are alkoxy groups, and most preferred is the bis(ethoxy)methane group, which has the chemical formula —CH$_2$—CH$_2$—O—CH$_2$—O—CH$_2$—CH$_2$—. A preferred alpha, omega dihalo organic compound is bis(2-chloroethyl) formal. More preferred is a combination of bis(2-chlorethyl) formal and 1,6-dichlorohexane.

In the present invention, an optional ingredient is at least one trihalo organic compound. Preferred are trihalo alkyl compounds, and more preferred is trihalo propane. Suitable halogens are chlorine, bromine, and iodine, with chlorine being the preferred halogen. In one embodiment, the preferred trihalo organic compound is 1, 2, 3-trichloropropane. A suitable amount of the trihalo organic compound or compounds is 0 to 10 mole % based on the moles of the alpha, omega dihalo organic compound or compounds; preferably 1 to 5 mole %, and more preferably 1.8 to 2.2 mole %. The trihalo organic compound or compounds, if used, is preferably mixed with the alpha, omega dihalo organic compound or compounds so that the mixed halo compounds are added together to the reaction mixture.

The liquid polysulfides of the present invention are believed to be formed by the chemical reaction among sodium polysulfide; the alpha, omega dihalo organic compound or compounds; and the optional trihalo compound or compounds. It has been found that this reaction, when performed in the presence of a phase transfer catalyst, surprisingly yields polysulfides that are liquid and are believed to be of relatively low molecular weight.

It is believed that the reaction between Na$_2$S$_n$ and the alpha, omega dihalo organic compound or compounds produces a polysulfide with the general chemical formula

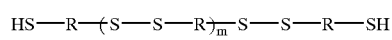

In this formula, m represents the degree of polymerization. If a trihalo organic compound is used, it is believed that the resulting structure is a branched polymer. If multiple dihalo organic compounds are used, with R groups denoted R, R', R", etc., the resulting polymer is believed to be a statistical copolymer of the repeat units SSR, SSR', SSR", etc.

The present invention can be practiced using a very wide variety of methods of adding the ingredients together and reacting them. It is possible to practice the present invention by combining all of the ingredients, except for the optional additional portion of sulfur, and heating them together to produce liquid polysulfide. The order of adding and reacting the various ingredients may be chosen by the practitioner, as long as the PTC is present when the sodium polysulfide reacts with the alpha, omega dihalo organic compound or compounds and with the optional trihalo organic compound or compounds.

In one embodiment of the present invention, some sodium polysulfide is formed and reacts with alpha, omega dihalo organic compound and optional trihalo organic compound while more sodium polysulfide is forming. In a preferred embodiment of the present invention, all of the sodium polysulfide is formed before the reaction among the sodium polysulfide, the alpha, omega dihalo organic compound or compounds, and the optional trihalo organic compound or compounds begins. In this preferred embodiment, the PTC may be present during the formation of the sodium polysulfide or it may be added after the completion of the formation of the sodium polysulfide.

A more preferred embodiment of the present invention is herein called the "sequential" embodiment, which is described in the following paragraphs.

The first step of the sequential embodiment of the present invention is to mix the aqueous solution of NaSH with sulfur. It is preferred to stir this mixture vigorously. It is also preferred to regulate the temperature of the mixture at approximately 30° C. More preferred is to simultaneously stir the mixture vigorously and regulate the temperature at approximately 30° C. It is preferred to allow this mixture to remain heated and stirred until the sulfur powder appears to dissolve and the reaction mixture appears to turn to a dark orange red color.

In the sequential embodiment of the present invention, the PTC may be added to the reaction mixture before, during, or after the reaction between the sulfur and NaSH takes place. It is preferred to first prepare the reaction mixture, then allow the NaSH and sulfur to appear to react, as described above, and then to add the PTC. It is preferred to stir the mixture before, during, and after the addition of the FTC. It is also preferred to adjust the temperature of the mixture to approximately 80° C. before adding the PTC and to maintain the temperature at approximately 80° C. after adding the PTC while the mixture continues to stir for approximately 1 minute to approximately 1 hour. More preferred is to continue the stirring at 80° C. for 10 minutes to 30 minutes.

In the next step of the sequential embodiment of the present invention, the alpha, omega dihalo organic compound or compounds (together with the trihalo organic compound or compounds, if used) is gradually added to the reaction mixture. A suitable addition method is to add the alpha, omega dihalo organic compound or compounds at a steady rate, where the rate is adjusted to require from 5 minutes to 10 hours to add all of the alpha, omega dihalo organic compound or compounds to the reaction mixture. Preferably the addition rate would be adjusted to require 0.5 to 5 hours to complete the addition; most preferably adjusted to require 1 to 3 hours. It is preferable to maintain the temperature at 60 to 120° C. during this gradual addition; it more preferable to maintain the temperature at 80 to 110° C. It is preferred to stir the reaction mixture throughout the addition of the alpha, omega dihalo organic compound or compounds. After the addition of the alpha, omega dihalo organic compound or compounds is complete, it is preferable to hold the reaction mixture at temperature of from 90 to 110° C. with continued stirring for 1 to 10 hours.

After the hold period, in the sequential embodiment of the present invention, an optional further amount of sulfur powder is added to the reaction mixture. To define the suitable amount of further sulfur to add, we define "total halo moles" as the total of the moles of alpha, omega dihalo organic compound or compounds and the moles of trihalo organic compound or compounds. A suitable amount of further sulfur to add is up to 1.0 mole of additional sulfur for each 1.0 total halo moles. Preferred is 0.1 to 1.0 mole of additional sulfur for each 1.0 total halo moles, and most preferred is 0.15 to 0.25 mole of additional sulfur for each 1.0 total halo moles. It is preferred to continue stirring the reaction mixture while adding the additional sulfur.

In the sequential embodiment of the present invention, it is preferred to hold the reaction mixture at elevated temperature with stirring for some time after the addition of the additional sulfur. Preferred temperature for this hold period is from 90 to 110° C. It is preferred to continue the stirring through this hold period. A suitable duration for this hold period is from 10 minutes to 2 hours. Preferred is from 0.5 to 1.5 hours.

This concludes the description of the sequential embodiment of the present invention.

After the liquid polysulfide of the present invention is formed, it can be isolated by techniques that are known in the chemical arts. Salts and other solid impurities may be removed by filtration of the reaction mixture; then the liquid polysulfide may be washed with water; and the water may be separated from the liquid polysulfide by decanting, gravity separation, or other means. We contemplate that such a simple procedure of filtration followed by washing and separating would be suitable for use in large scale manufacturing of liquid polysulfide.

If the practitioner of the present invention desires an especially pure product, for example for laboratory analysis, the following high-purity method of isolation may be employed. The reaction mixture can be washed with water, and the water can be removed with a rotary evaporator. A preferred amount of water for washing is 2 to 5 times the volume of the reaction mixture. The rotary evaporation is preferably conducted under partial vacuum at 80 to 100° C. The liquid polysulfide can then be dissolved in an organic solvent and filtered. A suitable solvent is methylene chloride, and a suitable amount is 0.1 to 2.0 times the volume of the reaction mixture. A suitable filtration method is vacuum filtration with Dicalite™ 4200, a diatomite filtration aid supplied by Grefco Inc., over filter paper. The filtrate can then be stripped; a suitable method is rotary evaporation under partial vacuum at 80 to 100° C.

Because of the potential for evolution of hydrogen sulfide, it may be suitable to use a scrubber during manufacturing, maintenance, and cleanout procedures involving the process of the present invention.

An advantage of the present invention is that the practitioner can conveniently control the molecular weight of the liquid polysulfide by any of three alternative methods. First, in any embodiment in which the sodium polysulfide is formed by reacting sulfur with sodium hydrosulfide, increasing the mole ratio of sulfur to NaSH will yield liquid polysulfides of higher molecular weight. Also, higher molecular weights of liquid polysulfides will be obtained in any embodiment in which the sodium polysulfide is formed by reacting sulfur with sodium hydrosulfide by increasing the ratio of total halo moles to the sum of moles of NaSH and moles of sulfur used during the production of the liquid polysulfide. A third method of controlling the molecular weight can be used in any embodiment in which the further portion of sulfur is added after the formation of the liquid polysulfide, since reaction of this further portion of sulfur with the liquid polysulfide raises the molecular weight of the liquid polysulfide.

One common use of the liquid polysulfides of the present invention is as an ingredient in cured rubbery solids. These cured solids are often used as sealants. One suitable method of curing the liquid polysulfide is to react it with manganese dioxide and a basic amine catalyst. One suitable type of basic amine catalyst is a tertiary amine catalyst. Among tertiary amine catalysts, a preferred catalyst is tris (dimethylaminomethyl) phenol. Another suitable type of basic amine catalyst is a thiuram compound. Thiuram compounds have the chemical structure

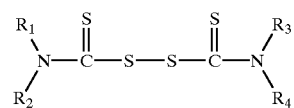

where $R_1$, $R_2$, $R_3$, and $R_4$ are organic groups. Among thiuram compounds, $R_1$, $R_2$, $R_3$, and $R_4$ are preferably alkyl groups, and most preferably all methyl groups.

It is to be understood that for purposes of the present specification and claims that the range and ratio limits recited herein can be combined. For example, if ranges of 60 to 120 and 80 to 110 are recited for a particular parameter, it is understood that the ranges of 60 to 110 and 80 to 120 are also contemplated.

EXAMPLES

In the following examples, the following test methods were used:

Carbon-13 NMR: The liquid polysulfide polymer was analyzed by $^{13}$C Nuclear Magnetic Resonance (NMR) spectroscopy. When the alpha, omega dihalo organic compound was bis(2-chloroethyl) formal, as in Example 1, we examined the spectrum at 38.8 to 39.0 ppm. The presence of a strong peak verified the preponderance of monomer units with the disulfide link. When the alpha, omega dihalo organic compounds were bis(2-chloroethyl) formal and 1,6-dichlorohexane, as in Example 2, we examined the spectrum at 38.6 to 38.8 ppm. The presence of a strong peak verified the preponderance of monomer units with the disulfide link. Details of this testing have been described by W. Mazurek and A. G. Moritz in *Macromolecules* volume 24, pages 3261–3265, 1991.

Curability: To test that the liquid polysulfide can be cured to form a suitable solid, a curing paste was made by mechanically mixing 48.25 gram Santicizer™ 278, a plasticizer from Solutia, Inc.; 278.25 gram of manganese dioxide; and 1.5 grams of tetramethylthiuram disulfide. Then 6 gram of the curing paste is mechanically mixed for about 24 seconds with 30 gram of liquid polysulfide and approximately 2 drops of water. The mixture is poured into a rectangular mold and allowed to stand at room temperature. After approximately 4 hours, the cake is removed from the mold, the edges are cut to form a rectangular block, and Shore A hardness is measured on one of the cut surfaces. If the material fails to form a cake, or if the Shore A hardness value is less than 10, the material is said to fail the curability test. Values of Shore A above 10 are acceptable, though typical sealant formulations show values of Shore A of 40 or more.

Example 1

A 3-liter round-bottomed flask was fitted with heating mantle, reflux condenser, mechanical stirrer, thermocouple, and an inlet for tubing from a peristaltic pump. The outlet of the reflux condenser was connected to a pair of 2-liter Erlenmeyer flasks, one of which was charged with 122.3 gram sodium hydroxide pellets and 1020.5 gram water. The round-bottomed flask was charged in succession with 1323.9 gram of sodium hydrosulfide aqueous solution (32.53% by weight sodium hydrosulfide, based on the total weight of the solution, filtered through Dicalite™ 4200, a diatomite filtration aid supplied by Grefco Inc., and glass fiber filter paper) and 61.6 gram of sulfur powder. The suspension was stirred at approximately 500 rpm and warmed to a target temperature of 80° C. As the temperature reached approximately 30° C., the sulfur appeared to dissolve, and bubbles believed to be hydrogen sulfide were observed to form. The solution turned from yellow to dark orange red, typical of polysulfide formation. When the temperature reached approximately 80° C., 1.0 gram of Aliquat™ 175 (supplied by Henkel, methyltributylammonium chloride, as a solution in water with concentration of 75% based on total weight of the solution) was added.

The solution was kept at 80° C. and stirred for 12 minutes, and then addition of the solution of halo compounds was begun. The solution of halo compounds was 8.9 gram of 1,2,3-trichloropropane dissolved in 508.8 gram of bis(2-chloroethyl) formal. Addition of the solution of halo compounds continued at a constant rate for approximately 1 hour, until all of the solution was added. During the addition, the reaction temperature ranged from 80.5 to 100.4° C. After the addition was complete, the reaction temperature was brought to 100° C. and held there, with stirring, for 4.5 hours. Then a second portion of sulfur (19.3 gram) was added over 3 minutes, during which formation of bubbles and foaming were observed. The viscosity of the reaction mixture appeared to rise after the addition of the sulfur was complete. The reaction mixture was kept at 100° C. with stirring for an additional 1 hour.

The resulting liquid polymer was washed three times, each time with 2 liters of water. The washed liquid polymer was stripped in a rotary evaporator at 90° C. under vacuum. The liquid polymer was then dissolved in 500 milliliters of methylene chloride, and the solution was filtered through a Buchner funnel over Dicalite™ 4200 and Whatman™ #1filter paper. The filtrate was stripped in a rotary evaporator at 90° C. under vacuum. The resulting product was 459 gram of pale yellow oil.

The oil could be readily poured at room temperature and was obviously liquid. The $^{13}$C NMR analysis verified that the oil did have a preponderance of monomer units that contained the disulfide link. Also, the liquid polysulfide of this example gave acceptable results in the curability test.

Example 2

A 3-liter round-bottomed flask was fitted with heating mantle, reflux condenser, mechanical stirrer, thermocouple, and an inlet for tubing from a peristaltic pump. The outlet of the reflux condenser was connected to a pair of 2-liter Erlenmeyer flasks, one of which was charge with 122.3 gram sodium hydroxide pellets and 1020.5 gram water. The round-bottomed flask was charged in succession with 1323.0 gram of sodium hydrosulfide aqueous solution (32.53% by weight sodium hydrosulfide, based on the total weight of the solution, filtered through Dicalite™ 4200 and glass fiber filter paper) and 61.8 gram of sulfur powder. The suspension was stirred at approximately 500 rpm and warmed to a target temperature of 80° C. As the temperature reached approximately 30° C., the sulfur appeared to dissolve, and bubbles believed to be hydrogen sulfide were observed to form. The solution turned from yellow to dark orange red, typical of polysulfide formation. When the temperature reached approximately 80° C., 9.4 gram of Aliquat™ 175 (supplied by Henkel, methyltributylanunonium chloride, as a solution in water with concentration of 75% based on total weight of the solution) was added.

The solution was kept at 80° C. and stirred for 12 minutes, and then addition of the solution of halo compounds was begun. The solution of halo compounds was 8.9 gram of 1,2,3-trichloropropane dissolved in 300.7 gram of 1,6-dichlorohexane and 173.1 gram of bis(2-chloroethyl) formal. Addition of the solution of halo compounds continued at a constant rate for approximately 1 hour, until all of the solution was added. During the addition, the reaction temperature ranged from 80.5 to 100.4° C. After the addition was complete, the reaction temperature was brought to 100° C. and held there, with stirring, for 4.5 hours. Then a second portion of sulfur (16.3 gram) was added all at once, after which formation of bubbles and foaming were observed. The viscosity of the reaction mixture appeared to rise after the addition of the sulfur was complete. The reaction mixture was kept at 100° C. with stirring for an additional 1 hour.

The resulting liquid polymer was washed three times; each wash was with a 2-liter volume of water. The washed liquid polymer was stripped in a rotary evaporator at 90° C. under vacuum. The liquid polymer was then dissolved in 500 milliliters of methylene chloride, and the solution was filtered through a Buchner funnel over Dicalite™ 4200 and Whatman™ #1 filter paper. The filtrate was stripped in a rotary evaporator at 90° C. under vacuum. The resulting product was 459 gram of pale yellow oil.

The oil could be readily poured at room temperature and was obviously liquid. The $^{13}C$ NMR analysis verified that the oil did have a preponderance of monomer units that contained the disulfide link. Also, the liquid polysulfide of this example gave acceptable results in the curability test.

We claim:

1. A process for making liquid polysulfide compositions comprising reacting sodium polysulfide; at least one alpha, omega dihalo organic compound; and optionally at least one trihalo organic compound in the presence of a phase transfer catalyst; wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy groups; wherein the halogen atoms of said alpha, omega dihalo organic compound are selected from the group consisting of chlorine, bromine, and iodine.

2. The process of claim 1, wherein said phase transfer catalyst is methyltributylammonium chloride, said alpha, omega dihalo organic compound comprises bis(2-chloroethyl) formal, and said trihalo organic compound is 1,2,3-trichloropropane.

3. A process for making liquid polysulfide compositions comprising reacting sodium polysulfide; at least one alpha, omega dihalo organic compound; and optionally at least one trihalo organic compound; wherein said reacting is performed in the presence of a phase transfer catalyst; wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy groups; wherein the halogen atoms of said alpha, omega dihalo organic compound are selected from the group consisting of chlorine, bromine, and iodine; and wherein said sodium polysulfide is formed by reacting sulfur and an aqueous solution of sodium hydrosulfide.

4. The process of claim 3, wherein said phase transfer catalyst is methyltributylammonium chloride, said alpha, omega dihalo organic compound comprises bis(2-chloroethyl) formal, and said trihalo organic compound is 1,2,3-trichloropropane.

5. A process for making liquid polysulfide compositions comprising
  (a) reacting sulfur and an aqueous solution of sodium hydrosulfide to form sodium polysulfide,
  (b) forming a liquid polysulfide by reacting said sodium polysulfide, at least one alpha, omega dihalo organic compound, and optionally at least one trihalo organic compound; wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy groups; wherein the halogens of said alpha, omega dihalo organic compound are selected from the group consisting of chlorine, bromine, and iodine; and wherein said reacting is performed in the presence of a phase transfer catalyst; and
  (c) optionally reacting said liquid polysulfide with additional sulfur to raise the molecular weight of said liquid polysulfide.

6. The process of claim 5, wherein the phase transfer catalyst is methyltributylammonium chloride.

7. The process of claim 5, wherein the alpha, omega dihalo organic compound comprises bis(2-chloroethyl) formal.

8. The process of claim 5, wherein the phase transfer catalyst is methyltributylammonium chloride, the alpha, omega dihalo organic compound comprises bis(2-chloroethyl) formal, and the trihalo organic compound is 1,2,3-trichloropropane.

9. A liquid polysulfide composition made by the process comprising reacting sodium polysulfide, at least one alpha, omega dihalo organic compound, and optionally at least one trihalo organic compound in the presence of a phase transfer catalyst; wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy groups; wherein the halogen atoms of said alpha, omega dihalo organic compound are selected from the group consisting of chlorine, bromine, and iodine.

10. The composition of claim 9, wherein the phase transfer catalyst is methyltributylammonium chloride, the alpha, omega dihalo organic compound comprises bis(2-chloroethyl) formal, and the trihalo organic compound is 1,2,3-trichloropropane.

11. A liquid polysulfide composition made by the process comprising
  (a) reacting sulfur and an aqueous solution of sodium hydrosulfide to form sodium polysulfide;
  (b) forming a liquid polysulfide by reacting said sodium polysulfide, at least one alpha, omega dihalo organic compound, and optionally at least one trihalo organic compound; wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy groups; wherein the halogens of said alpha, omega dihalo organic compound are selected from the group consisting of chlorine, bromine, and iodine; and wherein said reacting is performed in the presence of a phase transfer catalyst; and
  (c) optionally reacting said liquid polysulfide with additional sulfur to raise the molecular weight of said liquid polysulfide.

12. The composition of claim 11, wherein the phase transfer catalyst is methyltributylammonium chloride, the alpha, omega dihalo organic compound comprises bis(2-chloroethyl) formal, and the trihalo organic compound is 1,2,3-trichloropropane.

13. A solid polysulfide composition useful as a sealant made by a process comprising curing a liquid polysulfide composition made by the process comprising reacting sodium polysulfide, at least one alpha, omega dihalo organic compound, and optionally at least one trihalo organic compound in the presence of a phase transfer catalyst; wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy groups; wherein the halogen atoms of said alpha, omega dihalo organic compound are selected from the group consisting of chlorine, bromine, and iodine.

14. A solid polysulfide composition useful as a sealant made by a process comprising curing a liquid polysulfide composition made by the process comprising reacting sodium polysulfide, at least one alpha, omega dihalo organic compound, and optionally at least one trihalo organic compound; wherein said reacting is performed in the presence of a phase transfer catalyst; wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy groups; wherein the halogen atoms of said alpha, omega dihalo organic compound are selected from the group consisting of chlorine, bromine, and iodine; and wherein said curing comprises reacting said liquid polysulfide with manganese dioxide and a basic amine compound.

15. A solid polysulfide composition useful as a sealant made by a process comprising curing a liquid polysulfide composition made by a process comprising:
  (a) reacting sulfur and an aqueous solution of sodium hydrosulfide to form sodium polysulfide;
  (b) forming a liquid polysulfide by reacting said sodium polysulfide, at least one alpha, omega dihalo organic compound, and optionally at least one trihalo organic compound; wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy group; wherein the halogens of said alpha, omega dihalo organic compound are selected from the group consisting of chlorine, bromine, and iodine; and wherein said reacting is performed in the presence of a phase transfer catalyst; and
  (c) optionally reacting said liquid polysulfide with additional sulfur to raise the molecular weight of said liquid polysulfide.

16. The composition of claim 15, wherein said curing comprises reacting said liquid polysulfide with manganese dioxide and a basic amine compound.

17. A sealant comprising a cured liquid polysulfide composition, wherein said liquid polysulfide is made by a process comprising reacting sodium polysulfide, at least one alpha, omega dihalo organic compound, and optionally at least one trihalo organic compound in the presence of a phase transfer catalyst; wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy groups; wherein the halogen atoms of said alpha, omega dihalo organic compound are selected from the group consisting of chlorine, bromine, and iodine.

18. A process for making liquid polysulfide compositions comprising mixing sodium polysulfide, at least one alpha, omega dihalo organic compound, and optionally at least one trihalo organic compound; after mixing is complete, reacting the polysulfide and the organic compound(s) for 1 to 10 hours, wherein said reacting is performed in the presence of a phase transfer catalyst, wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy groups, and wherein the halogen atoms of said alpha, omega dihalo organic compound are selected from the group consisting of chlorine, bromine, and iodine.

19. A liquid polysulfide composition made by the process comprising mixing sodium polysulfide, at least one alpha, omega dihalo organic compound, and optionally at least one trihalo organic compound; after mixing is complete, reacting the polysulfide and the organic compound(s) for 1 to 10 hours, wherein said reacting is performed in the presence of a phase transfer catalyst, wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy groups, and wherein the halogen atoms of said alpha, omega dihalo organic compound are selected from the group consisting of chlorine, bromine, and iodine.

20. A solid polysulfide composition useful as a sealant made by a process comprising curing a liquid polysulfide composition made by the process comprising mixing sodium polysulfide, at least one alpha, omega dihalo organic compound, and optionally at least one trihalo organic compound; after mixing is complete, reacting the polysulfide and the organic compound(s) for 1 to 10 hours, wherein said reacting is performed in the presence of a phase transfer catalyst, wherein the group between the halogen atoms of said alpha, omega dihalo organic compound is selected from the group consisting of alkyl groups of 3 or more carbon atoms, aryl groups, alkylaryl groups, alkyloxy groups, and arylalkoxy groups, and wherein the halogen atoms of said alpha, omega dihalo organic compound are selected from the group consisting of chlorine, bromine, and iodine.

21. A sealant comprising a cured liquid polysulfide composition, wherein said liquid polysulfide is made by a process comprising mixing sodium polysulfide, at least one alpha, omega dihalo organic compound, and optionally at least one trihalo organic compound; after mixing is complete, reacting the polysulfide and the organic compound(s) for 1 to 10 hours, wherein said reacting is performed in the presence of a phase transfer catalyst, wherein the group between the halogen atoms of said alpha, omega dihalo organic compound is selected from the group consisting of alkyl groups 3 or more carbon atoms, aryl groups, alkylaryl groups, alkyloxy groups, and arylalkoxy groups, and wherein the halogen atoms of said alpha, omega dihalo organic compound are selected from the group consisting of chlorine, bromine, and iodine.

22. The process of claim 1, comprising 0.10–10 mole % of the phase transfer catalyst based on the moles of the one alpha, omega dihalo organic compound.

* * * * *